United States Patent [19]
Lysenko et al.

[11] Patent Number: 4,486,608
[45] Date of Patent: Dec. 4, 1984

[54] PREPARATION OF MONO- AND DIBROMO- OR CHLOROALDEHYDES

[75] Inventors: Zenon Lysenko; Richard G. Pews, both of Midland, Mich.

[73] Assignee: The Dow Chemical Company, Midland, Mich.

[21] Appl. No.: 487,476

[22] Filed: Apr. 22, 1983

Related U.S. Application Data

[63] Continuation-in-part of Ser. No. 360,530, Mar. 22, 1982, abandoned.

[51] Int. Cl.$^3$ .................. C07C 45/63; C07C 47/14
[52] U.S. Cl. ............................................ 568/466
[58] Field of Search .............................. 568/466, 841

[56] References Cited

U.S. PATENT DOCUMENTS

| 2,478,741 | 8/1949 | Brothman | 568/466 |
| 2,697,120 | 12/1954 | Gilbert | 568/466 |
| 2,702,303 | 2/1954 | Otto | 568/466 |
| 2,863,924 | 12/1958 | Pianfetti et al. | 568/466 |
| 3,240,813 | 3/1966 | Dick | 568/466 |
| 3,636,102 | 1/1972 | Lippman | 568/466 |

FOREIGN PATENT DOCUMENTS 770182 10/1967 Canada ............................ 568/466

OTHER PUBLICATIONS

Patai, "The Chemistry of Acyl Halides", Interscience Pub., NY, (1972), pp. 55–56.

Primary Examiner—Werren B. Lone

[57] ABSTRACT

A process for making mono- and dichlorinated or brominated aldehydes from aldehydes having at least 3 carbon atoms and hydrogens alpha to the carbonyl group or primary alcohols having at least 3 carbon atoms and hydrogens in the 2-position by direct bromination or chlorination by carrying out the bromination or chlorination in an inert organic solvent with bromine or chlorine and containing a catalyst complex of HX and an N,N-dialkyl or cycloalkylformamide where X is a counterion.

12 Claims, No Drawings

PREPARATION OF MONO- AND DIBROMO- OR CHLOROALDEHYDES

CROSS REFERENCE TO RELATED APPLICATION

This application is a continuation-in-part of U.S. Application Ser. No. 360,530, filed Mar. 22, 1982, now abandoned.

BACKGROUND OF THE INVENTION

De Buyck et al., Bull. Soc. Chim. Belg. 89 (1980) pp. 441 ff teach the preparation of 2,2-dichloroaldehydes from aldehydes and alcohols by chlorination in dimethylformamide. This reference teaches that induction periods are minimized by the addition of 5 to 10 percent dry hydrogen chloride and that the use of dimethyl formamide as a solvent imparts beneficial stability to the reactants to form the products free of undesirable side reactions.

While the process is effective, it has been found that the dimethylformamide, an expensive solvent, could not be reused as the solubility of chlorine was markedly reduced upon completing only one reaction, the DMF recovery was poor and therefor fresh dimethylformamide had to be added.

SUMMARY OF THE INVENTION

This invention provides a process for making mono- and dichlorinated or mono- or dibrominated aldehydes from aldehydes having at least 3 carbon atoms and having hydrogens alpha to the carbonyl group or primary alcohols having at least 3 carbon atoms and having hydrogens in the 2-position by direct bromination or chlorination which comprises carrying out the bromination or chlorination in an organic solvent with bromine or chlorine and containing a catalyst consisting essentially of a complex of HX and an N,N-dialkyl or cycloalkylformamide, where X is a counterion. Preferably X is a counterion of a mineral acid and most preferably is Cl or Br. The reaction is generally carried out in the presence of an inert organic solvent containing liquid bromine or chlorine gas and the desired aldehyde or alcohol and bromine or chlorine are added while agitating the reaction mixture. It has further been found that this catalyst can be reused or recovered without any need of regeneration. In addition, it has also been shown that the reaction may be carried out in the product aldehyde as the solvent without using any other solvent.

Detailed Description of the Invention

The preferred catalysts are the DMF/HCl and DMF/HBr complexes and they are prepared by sparging HCl or HBr into DMF at any temperature from the melting point to the boiling point of the amide, preferably 40° to 70° C. The complex may be used directly or the saturated solution may be allowed to stand an additional 12 to 16 hours or so at ambient temperature to obtain the complex in crystalline form. The crystalline complex may be used directly without further purification.

The reaction medium may be two phase or single phase. Inert solvents such as, for example, carbon tetrachloride and tetrachloroethane may be employed, but the product aldehyde itself is the preferred solvent. The aldehydes and alcohols may be chlorinated or brominated at any temperature from 0° to 80° C., preferably 40° to 60° C.

In the process of this invention, side reactions, e.g., aldol condensation, over bromination or chlorination and/or oxidation to carboxylic acids and/or acid chlorides, are not present and the product may be obtained free of undesirable contaminants by fractional distillation.

The brominated or chlorinated aldehydes prepared by the process of this invention are useful intermediates for the synthesis of halogenated substituted pyridines, herbicides and pharmaceutical monomers.

The invention is further illustrated by the following examples.

EXAMPLE 1

Preparation of the DMF/HCl complex

Dimethylformamide (DMF) was stirred in a 250 ml three necked round bottomed flask equipped with an HCl inlet tube. HCl was sparged into the DMF at such a rate as to maintain the temperature between 50° and 70° C. for a period of 30 minutes. Upon completion of the addition, the saturated solution was allowed to react overnight at room temperature. The resulting crystalline complex was used as such without further purification.

EXAMPLE 2

Preparation of 1-pyrrolidine carboxaldehyde—HCl complex

25 Grams (g) (0.25 mole) of 1-pyrrolidine carboxaldehyde was placed in a 100 ml three necked flask and kept at room temperature by means of an ice-water bath. HCl gas was passed into the reaction for a period of 7 minutes, during which time the temperature rose to 81° C. The reactants solidified and excess HCl was removed in vacuo to afford 34 g of a white crystalline complex which was used without further purification.

EXAMPLE 3

Preparation of N,N-diethylformamide—HCl complex

A quantity of 100 g (~1.0 mole) of N,N-diethylformamide was placed in a 250 ml three necked flask in an ice bath. HCl gas was sparged through the reaction mixture for a period of 25 minutes during which time the temperature rose to 110° C. and cooled back to 20° C. Upon completion of the addition, the unreacted HCl was removed in vacuo to afford 135 g of the DEF/HCl complex which was isolated as a pale yellow oil and used without any further purification.

EXAMPLE 4

Preparation of 2,2-dichloropropionaldehyde (single phase preparation)

A quantity of 75 ml of the above prepared DMF/HCl complex was added to a three necked 500 ml flask containing 100 ml of 1,1,2,2-tetrachloroethane and the solution was saturated with chlorine. Propionaldehyde (150 ml) was added dropwise to the stirred solution and chlorine addition was maintained in excess such that the temperature was kept between 50° and 70° C. An ice bath was kept nearby to control any undesirable exotherms.

Upon completion of the addition of propionaldehyde to the reaction, the product was stripped off in vacuo and collected in a dry ice trap. Distillation of the product afforded 175 g of 2,2-dichloropropionaldehyde, b.p. 83°–85° C., ~70 percent yield based on distilled product.

EXAMPLE 5

Preparation of 2,2-dichloropropionaldehyde (Recycle of DMF/HCl complex)

75 ml of the DMF/HCl complex used in Example 4 was added to a three necked 500 ml flask with 100 ml of 1,1,2,2-tetrachloroethane. 150 ml of propionaldehyde was added dropwise to the stirred solution presaturated with $Cl_2$. $Cl_2$ addition was maintained such that pot temperature was maintained between 50° and 70° C. Upon completion, the product was stripped off in vacuo and collected in a dry ice trap. Distillation afforded 175 g of 2,2-dichloropropionaldehyde, b.p. 83°–86° C., yield ≅70 percent.

EXAMPLE 6

Preparation of 2,2-dichloropropionaldehyde

A 2 liter, three necked, round bottomed flask, equipped with a thermal well, paddle stirrer and condenser, was charged with 77.4 g of the DMF/HCl complex dissolved in 200 ml of 1,1,2,2-tetrachloroethane. The reaction solution was made yellow with chlorine and propionaldehyde was added in such a manner as to maintain the temperature between 50° and 60° C. Addition was sustained until 860 ml of propionaldehyde (11.94 moles) was added. The total weight present in the flask upon completion of the addition of propionaldehyde was 1769.8 g having a 4.4 percent concentration of the DMF/HCl complex present in the solution. The product, 2,2-dichloropropionaldehyde, was stripped from the reaction mixture in vacuo and distilled to afford 1079 g of essentially pure 2,2-dichloropropionaldehyde.

EXAMPLE 7

Preparation of 2,2-dichloro-2-phenylacetaldehyde

To a three necked 500 ml flask containing 100 ml of $CCl_4$ was added 75 ml of DMF/HCl complex. The solution was presaturated with $Cl_2$ and phenylacetaldehyde (100 ml, 60 grams, 0.5 mole) was added dropwise concurrently with the steady addition of $Cl_2$. The temperature of the reaction rose to 55°–65° C. and was kept constant by the simultaneous addition of $Cl_2$ and aldehyde. Upon completion of the addition of the aldehyde, the chlorine addition was stopped. The reaction was poured into a one liter separatory funnel and the phases were allowed to separate. The lower layer containing the product was separated, the $CCl_4$ stripped off in vacuo and the 2,2-dichloro-2-phenylacetaldehyde was distilled to afford 69.8 g, b.p. 60°–70° C., at 4 mm Hg. The yield was 43.4 percent of essentially pure product.

EXAMPLE 8

Preparation of 2,2-dichlorovaleraldehyde

To a 500 ml three necked flask equipped with a mechanical stirrer, condenser, chlorine inlet tube and an addition funnel was added 75 ml of the DMF/HCl complex dissolved in 100 ml of $CCl_4$. Chlorine gas and valeraldehyde (80.2 g, ~0.93 mole) were added concurrently in such a manner as to maintain a slight excess of chlorine in the reaction mixture and to keep the temperature between 60° and 70° C. Upon completion of the addition, the reaction mixture separated into two layers. The lower $CCl_4$ layer was isolated by means of a separatory funnel and the solvent removed on a rotary evaporator. The crude 2,2-dichlorovaleraldehyde was distilled at 10 mm Hg. Three fractions were collected containing essentially pure 2,2-dichlorovaleraldehyde affording 144.2 g, 99.4 percent yield, b.p. 23°–30° C.

EXAMPLE 9

Preparation of 2,2-dichloroisovaleraldehyde

To a 1 liter flask containing 100 ml of the DMF/HCl complex in 200 ml of $CCl_4$ were added concurrently chlorine gas and isovaleraldehyde (240 g, 2.8 moles). The addition was kept such as to maintain a slight excess of chlorine throughout the reaction and to maintain the reaction temperature between 60° and 70° C. Phases were separated at the completion of the reaction and solvent was removed from the lower $CCl_4$ layer in vacuo. The resulting residue was distilled to afford 314 g (72.4 percent yield) of essentially pure 2,2-dichloroisovaleraldehyde, b.p. 30°–37° C. at 15 mm Hg.

EXAMPLE 10

Preparation of 2-chloro-2-methylbutyraldehyde

Chlorine gas and 2-methylbutyraldehyde (228.3 g, 2.65 moles) were added concurrently to a 1 liter, three necked flask containing 40 g of DMF/HCl catalyst dissolved in 100 ml of 1,1,2,2-tetrachloroethane. The temperature of the reaction was maintained by controlling the rates of the additions and by means of a water bath. Upon completion of the addition, the product was stripped from the reaction mixture in vacuo by means of a rotary evaporator and distilled to afford ~250 g (78 percent yield) of essentially pure 2-chloro-2-methylbutyraldehyde, b.p. 70°–75° C. at 68 mm Hg or 40°–48° C. at 6 mm Hg.

EXAMPLE 11

Preparation of 2-chloro-2-methylpropionaldehyde

Isobutyraldehyde (92.5 g, 1.28 moles) and $Cl_2$ gas were added concurrently to a three necked, 500 ml flask containing 40 g DMF/HCl complex and 100 ml of 1,1,2,2-tetrachloroethane. The temperature was maintained at 40° C. by controlling the rates of addition and by means of a water bath. Upon completion of the addition, the product was stripped from the reaction mixture in vacuo and distilled to 96.6 g (70.9 percent yield) of 2-chloro-2 methylpropionaldehyde.

EXAMPLE 12

Preparation of 2,2-dichlorobutyraldehyde from 1-butanol n-Butanol and $Cl_2$ were added concurrently to a 100 ml, four necked, round bottomed flask containing ~10 g of DMF/HCl catalyst and 25 ml of 1,1,2,2-tetrachloroethane. The temperature was maintained between 50° and 55° C. by controlling the rates of the addition. Upon completion of the addition, the reaction mixture was shown to contain mainly the product 2,2-dichlorobutyraldehyde by GC and NMR analysis. Similar results were obtained with isobutanol and 3-phenylpropanol. Analysis was in agreement with authentic products by GC, IR and NMR.

EXAMPLE 13

Preparation of 2,2-dichloropropionaldehyde using other catalysts

The procedure for the preparation of 2,2-dichloropropionaldehyde using 1-pyrrolidine carboxaldehyde/HCl and also the N,N-diethyl formamide/HCl was essentially the same as that used when the DMF/HCl complex was used as catalyst. Similar quantities were used for all examples. The yields were 72.5 and 89 percent, respectively.

EXAMPLE 14

Preparation of 2-bromo- and 2,2-dibromopropionaldehyde

A mixture of 50 ml CCl$_4$, 5.0 g of DMF/HCl catalyst and 40 g of liquid bromine was placed in a 500 ml round bottom flask and 36 ml of propionaldehyde (0.5 mole, 29 g) was added dropwise. The evaluation of HBr began immediately and the temperature of the reacting mixture rose to 60° C. The rate of addition of propionaldehyde was such as to maintain the temperature at 60°–70° C. After the addition of about 15 ml of propionaldehyde, 40 more grams of liquid bromine were added to the flask. After a total of 25 ml of propionaldehyde had been added, another addition of 40 grams of liquid bromine was made. Upon completion of the addition of the propionaldehyde, the bromine color had disappeared. Unreacted aldehyde, CCl$_4$ and HBr were removed under vacuum and the residue was distilled through a short path apparatus. Material boiling from 110° to 145° C. at 760 mm Hg was collected. Analysis by gas chromatography showed the presence of 10% 2-bromopropionaldehyde and 90% 2,2-dibromopropionaldehyde. The total yield was 46.5 grams of product as a yellow liquid (about 85% yield based on bromine added). The structure of the two products was confirmed by NMR.

Various modifications may be made in the present invention without departing from the spirit or scope thereof and it is understood that we limit ourselves only as defined in the appended claims.

We claim:

1. A process for making a member of the group consisting of mono- and dichlorinated and mono- and dibrominated aldehydes which comprises treating a member of the group consisting of aldehydes having at least 3 carbon atoms and having hydrogens alpha to the carbonyl group and primary alcohols having at least 3 carbon atoms and having hydrogens in the 2-position with a member of the group consisting of bromine and chlorine in an organic solvent containing a catalyst consisting essentially of a complex of HX and a member of the group consisting of N,N-dialkyl and cycloalkylformamide, where X is a counterion.

2. Process of claim 1 wherein the temperature is maintained at 0° to 80° C.

3. Process of claim 1 wherein X is a counterion of a mineral acid.

4. Process of claim 1 wherein X is Cl or Br.

5. Process of claim 4 wherein X is Cl, the aldehyde is propionaldehyde and the product is 2,2-dichloropropionalehyde.

6. Process of claim 4 wherein X is Br, the aldehyde is propionaldehyde and the product is 2,2-dibromopropionaldehyde.

7. Process of claim 6 wherein the aldehyde is phenylacetaldehyde and the product is 2,2-dichloro-2-phenylacetaldehyde.

8. Process of claim 4 wherein X is Cl, the aldehyde is valeraldehyde and the product is 2,2-dichlorovaleraldehyde.

9. Process of claim 4 wherein X is Cl, the aldehyde is isovaleraldehyde and the product is 2,2-dichloroisovaleraldehyde.

10. Process of claim 4 wherein X is Cl, the aldehyde is 2-methylbutyraldehyde and the product is 2-chloro-2-methylbutyraldehyde.

11. Process of claim 4 wherein X is Cl, the aldehyde is isobutyraldehyde and the product is 2-chloro-2-methylpropionaldehyde.

12. Process of claim 4 wherein n-butanol is reacted with chlorine and the product is 2,2-dichlorobutyraldehyde.

* * * * *